United States Patent [19]

Sakai et al.

[11] Patent Number: 4,464,388
[45] Date of Patent: Aug. 7, 1984

[54] USE OF PROSTAGLANDIN ANALOGUES TO TREAT CYTODAMAGE

[75] Inventors: Yoshiki Sakai, Osaka; Katsuhiro Imaki, Tsuzuki; Takashi Muryobayashi, Takatsuki, all of Japan

[73] Assignee: Ono Pharmaceutical Co., Ltd., Osaka, Japan

[21] Appl. No.: 478,031

[22] Filed: Mar. 23, 1983

[30] Foreign Application Priority Data

Mar. 25, 1982 [JP] Japan ................... 57-46380

[51] Int. Cl.³ .................. A61K 31/38; A61K 31/215; A61K 31/19
[52] U.S. Cl. ..................... 424/275; 424/285; 424/274; 424/305; 424/317
[58] Field of Search .............. 424/305, 317, 274, 285, 424/275

[56] References Cited

U.S. PATENT DOCUMENTS 4,215,142  7/1980  Hayashi et al. ............ 424/308
4,367,237  1/1983  Wakatsuka et al. ......... 424/275

Primary Examiner—Sam Rosen
Attorney, Agent, or Firm—Stevens, Davis, Miller & Mosher

[57] ABSTRACT

Prostaglandin analogue of the formula:

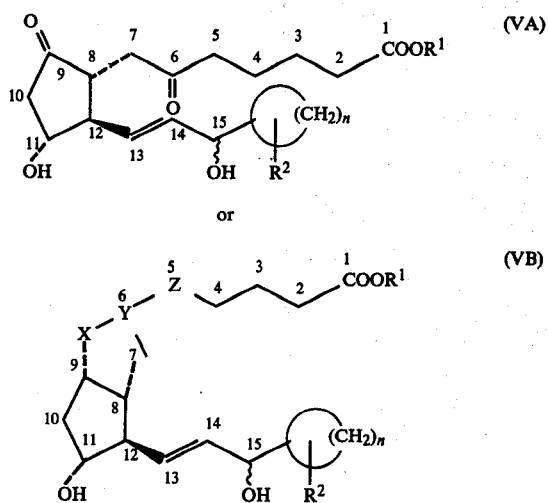

wherein $R^1$ represents a hydrogen atom or a straight- or branched-chain alkyl group containing from 1 to 12 carbon atom(s), $R^2$ represents a hydrogen atom or a straight- or branched-chain alkyl group containing from 1 to 6 carbon atom(s), the symbols———X—Y—Z— in formula VB represent one of the groups: t,0020 wherein in formulae (ii) and (iv), the configuration on $C_6$ is S- or R-configuration or a mixture thereof and in formulae (iii) and (v) the double bond between $C_5$ and $C_6$ is in E- or Z-configuration or a mixture thereof) and n represents an integer of from 3 to 5 non-toxic salts thereof when $R^1$ represents a hydrogen atom and cyclodextrin clathrates thereof are useful in the prevention or treatment of cytodamage associated with many diseases, especially liver damage.

30 Claims, No Drawings

USE OF PROSTAGLANDIN ANALOGUES TO TREAT CYTODAMAGE

DESCRIPTION

This invention relates to a new use of prostaglandin analogues, in the treatment of disease caused by cytodamage.

Prostaglandins are derivatives of prostanoic acid which has the following formula:

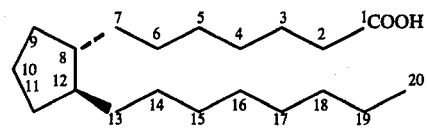

Various types of prostaglandins are known, the types depending inter alia on the structure and substituents on the alicyclic ring. For example, the alicyclic ring of prostaglandin E(PGE) has the structure:

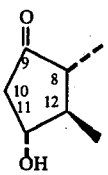

The dotted lines in the foregoing formulae and in other formulae throughout this specification denote, in accordance with generally accepted rules of nomenclature, that the attached grouping lies behind the general plane of the ring system, i.e. that the grouping is in α-configuration, and the thickened lines denote that the grouping lies in front of the general plane of the system; i.e. that the grouping is in β-configuration. The wavy line in other formulae throughout this specification indicates that the grouping is in α- or β-configuration or a mixture thereof.

Such compounds are sub-classified according to the position of double bond(s) in the side chain(s) attached to the 8- and 12-positions of the alicyclic ring. $PG_1$ compounds have a trans- double bond between $C_{13}-C_{14}$ (trans-$\Delta^{13}$). Prostaglandin $E_1$ ($PGE_1$) is characterised by the following structure (III):

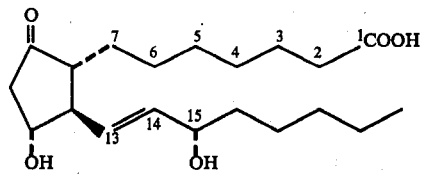

Moreover, when one or more methylene groups are eliminated from the aliphatic group attached to the 12-position of the alicyclic ring of the prostaglandins the compounds are known, in accordance with the usual rules of organic nomenclature, as nor-prostaglandins and, when more than one methylene group is eliminated, the number is indicated by di- tri- etc. before the prefix "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

PGE's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. $PGE_1$ inhibits blood platelet aggregation and also removes the thrombus and prevents thrombosis. PGE's have a stimulating effect on smooth muscle and increase the intestinal peristalsis; these actions indicate therapeutic utility on post-operative ileus and as purgatives. PGE's may also be used as oxytocics, as abortifacients in the first and second trimesters; in the post-labour abortion of the placenta, and as oral contraceptives because they regulate the sexual cycle of female mammals. PGE's have vasodilator and diuretic activities. They are useful for improvement in patients suffering from cerebral vascular disease because they increase the cerebral blood flow, and are also useful in the treatment of asthmatic conditions in patients because of their bronchodilating activity.

$PGI_2$ is a physiologically active substance having the following formula:

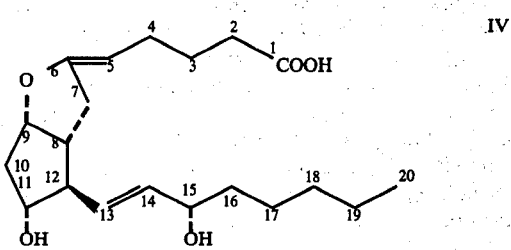

and its chemical name is (5Z,13E)-(9α,11α,15S)-6,9-epoxy-11, 15-dihydroxyprosta-5,13-dienoic acid (Nature, 263, 663 (1976), Prostaglandins, 12, 685 (1976), ibid, 12, 915 (1976), ibid, 13, 3 (1977), ibid, 13, 375 (1977) and Chemical and Engineering News, Dec. 20, 17 (1976)).

It is well known that $PGI_2$ can be prepared by incubation of prostaglandin $G_2$ ($PGG_2$) or prostaglandin $H_2$ ($PGH_2$) with microsomal fractions prepared from thoracic aorta of swine, mesenteric artery of swine, rabbit aorta or the stomach fundus of rats. $PGI_2$ has a relaxing activity on the artery, which is peculiar to the artery and which does not operate on other smooth muscle. Furthermore, $PGI_2$ strongly inhibits arachidonic acid-induced blood platelet aggregation of the human.

Taking into consideration that thromboxane $A_2$ prepared by incubation of $PGG_2$ or $PGH_2$ with blood platelet microsome, has a contracting activity on the artery and an aggregating activity on blood platelets, the properties of $PGI_2$ heretofore mentioned show that $PGI_2$ fulfils a very important physiological part in a living body. $PGI_2$ may be useful in the treatment of arteriosclerosis, cardiac failure or thrombosis.

Recently, it has been found that certain individual prostaglandin analogues have a previously unknown activity. This activity is to protect cells in the living body.

For example, it was reported by T. Manabe et al that $PGE_2$ was effective against a diet-induced acute pancreatitis in mice (cf. Gastroenterology, 78, 777–781 (1980)). It was reported by J. Stachur et al that 16,16-dimethyl-$PGE_2$ prevents acute galactosamine-induced liver damage and carbon tetrachloride-induced liver cell necrosis (cf. Folia Histochemica et Cytochemica, 18, 311–318 (1980) and Gastroenterology, 81, 211–217 (1981), respectively). Further, it was reported that $PGI_2$ prevents and is useful in treating hypoxia in the isolate perfused cat liver, endotoxin shock in dog, ischemic myocardial tissue in cat and endotoxin-induced lung injury in sheep (cf. H. Araki et al, Am. J. Physiol. 238, H176–H181 (1980), J. R. Fletcher et al, Circulatory Shock, 7, 299–308 (1980), H. Araki et al, Circulation Research, 47, No. 5, 757–763 (1980) and R. H. Demling et al, Surgery, 89, No. 2, 257–263 (1981), respectively).

Although the mechanism of the new activity is not yet clear, the activity is collectively named cytoprotective activity. It will be apparent from the above reports, that only a small number of individual prostaglandins or prostaglandin analogues have been found to have cytoprotective activity.

As a result of research and investigation it has been found that only a very limited number of, and not all, prostaglandin analogues have cytoprotective activity. In particular, it has surprisingly been discovered that certain prostaglandin compounds in which the n-pentyl group attached to the 15-position of the prostaglandin skeleton is replaced by a cycloalkyl group, having strong cytoprotective activity.

The present invention accordingly provides a method for the treatment (which may be preventive treatment) of cytodamage in a mammalian host, which comprises administering to a host suffering from, or subject to, cytodamage at least one prostaglandin analogue of the general formula:

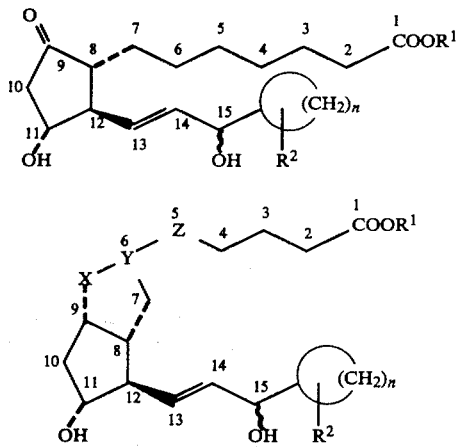

wherein $R^1$ represents a hydrogen atom or a straight- or branched-chain alkyl group containing from 1 to 12 carbon atom(s), $R^2$ represents a hydrogen atom or a straight- or branched-chain alkyl group containing from 1 to 6 carbon atom(s), the symbols —X—Y—Z— in formula VB represent one of the groups:

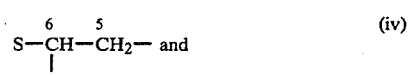

wherein in the formulae (ii) and (iv), the configuration on $C_6$ is S- or R-configuration or a mixture thereof, and in the general formulae (iii) and (v), the double bond between $C_5$ and $C_6$ is in E- or Z-configuration or a mixture thereof, n represents an integer of from 3 to 5, the double bond between $C_{13}$–$C_{14}$ is trans, and the hydroxy group attached to $C_{15}$ is in α- or β-configuration or a mixture thereof) or, when $R^1$ represents a hydrogen atom, non-toxic salt thereof, or cyclodextrin clathrate thereof.

15-Cycloalkyl-6-oxo-$PGE_1$ compounds represented by the general formula (VA), and their preparation are described in the specifications of Japanese Patent Kokai No. Showa 54-44639 and U.S. Pat. No. 4,215,142.

15-Cycloalkyl-6,9α-nitrilo-$PGI_1$ compounds represented by general formula (VB) wherein the symbols —X—Y—Z— represent a group of formula (i) and their preparation are described in the specifications of Japanese Patent Kokai No. Showa 54-125653 and U.S. Pat. No. 4,234,597. Cyclodextrin clathrates of such compounds may be prepared by known methods for the preparation of cyclodextrin clathrates of other prostagladin compounds.

15-Cycloalkyl-$PGI_1$ compounds represented by the general formula (VB) wherein the symbols —X—Y—Z— represent a group of formula (ii) and their preparation are described in the specifications of Japanese Patent Kokai No. Showa 53-95958 and United Kingdom Pat. No. 1598143.

15-Cycloalkyl-$PGI_2$ compounds represented by the general formula (VB) wherein the symbols —X—Y—Z— represent a group of formula (iii), and their preparation are described in the specifications of Japanese Patent Kokai No. Showa 53-103464 and 53-116365 and U.S. Pat. No. 4,178,367.

15-Cycloalkyl-6,9α-thio-$PGI_1$ compounds represented by the general formula (VB) wherein the symbols —X—Y—Z— represent a group of formula (iv), and their preparation are described in the specifications of Japanese Patent Kokai No. Showa 55-73678 and United Kingdom Patent Publication No. 2038815.

15-Cycloalkyl-6,9α-thio-$PGI_2$ compounds represented by the general formula (VB) wherein the symbols —X—Y—Z represent a group of formula (v), and their preparation are described in the specifications of Japanese Patent Kokai No. Showa 54-52069 and United Kingdom Patent Publication No. 2007218.

Although compounds represented by the general formulae (VA) and (VB) themselves are known, the fact that they have cytoprotective activity was heretofore unknown and there is no disclosure of such activity in the specifications referred to above.

In the general formulae (VA) and (VB), examples of the straight- or branched-chain alkyl groups containing from 1 to 12 carbon atom(s) represented by $R^1$ are methyl, ethyl, propyl, butyl, pentyl, hexyl, heptyl, octyl, nonyl, decyl, undecyl, dodecyl groups and isomers thereof, and preferred alkyl groups are methyl, ethyl, propyl, isopropyl, butyl, isobutyl, sec-butyl and tert-butyl groups. Compounds of general formulae VA and VB in which $R^1$ represents a hydrogen atom or a methyl group are especially preferred.

In the general formulae (VA) and (VB), examples of the cycloalkyl groups represented by the general formula:

are cyclobutyl, cyclopentyl and cyclohexyl groups; cyclopentyl is preferred.

In the general formulae (VA) and (VB), examples of the straight- or branched-chain alkyl groups containing from 1 to 6 carbon atom(s) represented by $R^2$ are methyl, ethyl, propyl, isopropyl, butyl, isobutyl, sec-butyl, tert-butyl groups and pentyl and hexyl groups and isomers thereof; preferably $R^2$ is a hydrogen atom or a methyl, ethyl, propyl, butyl, pentyl or hexyl group. More preferably $R^2$ represents a hydrogen atom or a propyl or butyl group. $R^2$ may be substituted on any position of the cycloalkyl ring; substitution on the 3- or 4-position of the cycloalkyl ring is preferred.

The hydroxy group attached to $C_{15}$ in formulae VA and VB is preferably in α-configuration.

Compounds of the general formula (VA) included in the present invention are as follows:
15-cyclobutyl-16,17,18,19,20-pentanor-6-oxo-PGE$_1$,
15-(3-ethylcyclobutyl)-16,17,18,19,20-pentanor-6-oxo-PGE$_1$,
15-(3-propylcyclobutyl)-16,17,18,19,20-pentanor-6-oxo-PGE$_1$,
15-cyclopentyl-16,17,18,19,20-pentanor-6-oxo-PGE$_1$,
15-(3-methylcyclopentyl)-16,17,18,19,20-pentanor-6-oxo-PGE$_1$,
15-(3-ethylcyclopentyl)-16,17,18,19,20-pentanor-6-oxo-PGE$_1$,
15-(3-propylcyclopentyl)-16,17,18,19,20-pentanor-6-oxo-PGE$_1$,
15-(4-methylcyclohexyl)-16,17,18,19,20-pentanor-6-oxo-PGE$_1$,
15-(4-ethylcyclohexyl)-16,17,18,19,20-pentanor-6-oxo-PGE$_1$ and
15-(4-propylcyclohexyl)-16,17,18,19,20-pentanor-6-oxo-PGE$_1$
and corresponding methyl esters thereof, non-toxic salts thereof and cyclodextrin clathrates thereof.

Compounds of the general formula (VB) included in the present invention are as follows:
15-cyclobutyl-16,17,18,19,20-pentanor-6,9α-nitrilo-PGI$_1$,
15-(3-propylcyclobutyl)-16,17,18,19,20-pentanor-6,9α-nitrilo-PGI$_1$,
15-(3-butylcyclobutyl)-16,17,18,19,20-pentanor-6,9α-nitrilo-PGI$_1$,
15-cyclopentyl-16,17,18,19,20-pentanor-6,9α-nitrilo-PGI$_1$,
15-(3-methylcyclopentyl)-16,17,18,19,20-pentanor-6,9α-nitrilo-PGI$_1$,
15-(3-ethylcyclopentyl)-16,17,18,19,20-pentanor-6,9α-nitrilo-PGI$_1$,
15-(3-propylcyclopentyl)-16,17,18,19,20-pentanor-6,9α-nitrilo-PGI$_1$,
15-(3-butylcyclopentyl)-16,17,18,19,20-pentanor-6,9α-nitrilo-PGI$_1$,
15-cyclohexyl-16,17,18,19,20-pentanor-6,9α-nitrilo-PGI$_1$,
15-(4-propylcyclohexyl)-16,17,18,19,20-pentanor-6,9α-nitrilo-PGI$_1$,
15-(4-butylcyclohexyl)-16,17,18,19,20-pentanor-6,9α-nitrilo-PGI$_1$,
15-cyclobutyl-16,17,18,19,20-pentanor-PGI$_1$,
15-(3-propylcyclobutyl)-16,17,18,19,20-pentanor-PGI$_1$,
15-(3-butylcyclobutyl)-16,17,18,19,20-pentanor-PGI$_1$,
15-cyclopentyl-16,17,18,19,20-pentanor-PGI$_1$,
15-(3-propylcyclopentyl)-16,17,18,19,20-pentanor-PGI$_1$,
15-(3-butylcyclopentyl)-16,17,18,19,20-pentanor-PGI$_1$,
15-cyclohexyl-16,17,18,19,20-pentanor-PGI$_1$,
15-(4-propylcyclohexyl)-16,17,18,19,20-pentanor-PGI$_1$,
15-(4-butylcyclohexyl)-16,17,18,19,20-pentanor-PGI$_1$,
15-cyclobutyl-16,17,18,19,20-pentanor-PGI$_2$,
15-(3-propylcyclobutyl)-16,17,18,19,20-pentanor-PGI$_2$,
15-(3-butylcyclobutyl)-16,17,18,19,20-pentanor-PGI$_2$,
15-cyclopentyl-16,17,18,19,20-pentanor-PGI$_2$,
15-(3-propylcyclopentyl)-16,17,18,19,20-pentanor-PGI$_2$,
15-(3-butylcyclopentyl)-16,17,18,19,20-pentanor-PGI$_2$,
15-cyclohexyl-16,17,18,19,20-pentanor-PGI$_2$,
15-(4-propylcyclohexyl)-16,17,18,19,20-pentanor-PGI$_2$,
15-(4-butylcyclohexyl)-16,17,18,19,20-pentanor-PGI$_2$,
15-cyclobutyl-16,17,18,19,20-pentanor-6,9α-thio-PGI$_1$,
15-(3-propylcyclobutyl)-16,17,18,19,20-pentanor-6,9α-thio-PGI$_1$,
15-(3-butylcyclobutyl)-16,17,18,19,20-pentanor-6,9α-thio-PGI$_1$,
15-cyclopentyl-16,17,18,19,20-pentanor-6,9α-thio-PGI$_1$,
15-(3-propylcyclopentyl)-16,17,18,19,20-pentanor-6,9α-thio-PGI$_1$,
15-(3-butylcyclopentyl)-16,17,18,19,20-pentanor-6,9α-thio-PGI$_1$,
15-cyclohexyl-16,17,18,19,20-pentanor-6,9α-thio-PGI$_1$,
15-(4-propylcyclohexyl)-16,17,18,19,20-pentanor-6,9α-thio-PGI$_1$,
15-(4-butylcyclohexyl)-16,17,18,19,20-pentanor-6,9α-thio-PGI$_1$,
15-cyclobutyl-16,17,18,19,20-pentanor-6,9α-thio-PGI$_2$,
15-(3-propylcyclobutyl)-16,17,18,19,20-pentanor-6,9α-thio-PGI$_2$,
15-(3-butylcyclobutyl)-16,17,18,19,20-pentanor-6,9α-thio-PGI$_2$,
15-cyclopentyl-16,17,18,19,20-pentanor-6,9α-thio-PGI$_2$,
15-(3-propylcyclopentyl)-16,17,18,19,20-pentanor-6,9α-thio-PGI$_2$,
15-(3-butylcyclopentyl)-16,17,18,19,20-pentanor-6,9α-thio-PGI$_2$,
15-cyclohexyl-16,17,18,19,20-pentanor-6,9α-thio-PGI$_2$,
15-(4-propylcyclohexyl)-16,17,18,19,20-pentanor-6,9α-thio-PGI$_2$,
15-(4-butylcyclohexyl)-16,17,18,19,20-pentanor-6,9α-thio-PGI$_2$, and corresponding methyl esters thereof, non-toxic salts thereof and cyclodextrin clathrates thereof.

The compounds of general formulae VA and VB and, when R' represents a hydrogen atom, non-toxic salts thereof, and cyclodextrin clathrates, possess strong cytoprotective activity and have low toxicity, as demonstrated by results given hereinafter. They may therefore be used in the treatment (including prevention treatment) of diseases associated with cell damage, especially liver damage. Their cytoprotective activity and low toxicity indicates utility in the treatment of many diseases as follows:

(1) digestive system diseases associated with cytodamage, for example:

(i) liver diseases such as acute yellow atrophy, fatty liver (especially of the alcoholic type), hepatic coma, hepatitis (especially of the alcoholic type, toxic type, hepatitis A or hepatitis B), hepatolenticular disease, hepatomegaly, portal hypertension, obstructive jaundice (especially cholestasis), liver abscess, liver cirrhosis (especially of the alcoholic type and biliary type), parasitic liver diseases, liver neoplasms and hepatic tuberculosis;

(ii) pancreatic diseases such as pancreatitis;

(iii) diseases of other digestive systems, eg biliary tract diseases such as biliary dyskinesia, cholangitis, oesophagal diseases, intestinal diseases such as enteritis, ileitis and proctitis, and stomach diseases;

(2) urologic diseases associated with cytodamage, for example:

(i) kidney diseases such as diabetic nephropathies, kidney cortex necrosis, acute kidney failure and nephrosclerosis;

(ii) diseases of other urologic systems such as cystitis and urethritis;

(3) respiratory tract diseases associated with cytodamage, for example:

(i) lung diseases such as obstructive lung diseases and pneumonia;

(ii) respiratory tract infections such as empyema, laryngitis, rhinitis and tracheitis;

(iii) other respiratory tract diseases such as respiration disorders and asthma;

(4) cardiovascular diseases associated with cytodamage, for example:

(i) heart diseases such as arrhythmia, and other coronary diseases, eg endocarditis;

(ii) cerebrovascular disorders such as cerebral aneurysm, cerebral embolism, cerebral hemorrhage and transient cerebral ischemia, (iii) microangiopathy such as retinopathy, nephropathy, neuropathy, (iv) diseases of other cardiovascular systems such as phlebitis, (5) haematologic diseases associated with cytodamage, for example: anaemia, bone marrow diseases, blood platelet disorders, splenic disorders, and (6) other diseases associated with cytodamage, for example; endocrine diseases such as diabetic Cushing's syndrome, Addison's disease, complications caused by diabetes mellitus, for example, microangiopathy such as retinopathy, nephropathy, neuropathy, immunologic diseases such as anaphylaxis, asthma, allergic vasculitis, and poisonings such as alcoholic poisoning, cadmium poisoning, carbon tetrachloride poisoning, lead poisoning, mercury poisoning and gas poisoning.

It has been reported that the results of liver function tests which are extensively used in clinics correlate fully with the findings of liver histological examination and liver cell damage, ie the degree of degeneration, necrosis and inflammation is accurately reflected in plasma glutamic oxaloacetic transaminase (GOT) and plasma glutamic pyruvic transaminase (GPT) levels. It is considered that drugs which suppress GOT and GPT activities in the experimental liver damage models described hereinafter are also effective in preventing or treating human liver damage, and in preventing or treating cell damage associated with other diseases and ailments.

The compounds of general formulae VA and VB will generally be used in the form of pharmaceutical compositions which comprise a compound of general formula VA or VB, or cyclodextrin clathrate thereof, or when $R^1$ in formula VA or VB represents a hydrogen atom, non-toxic salt thereof, together with a pharmaceutical carrier or coating.

In clinical practice, for the treatment of cytodamage, the compounds of formula VA or VB, or cyclodextrin clathrate or non-toxic salt thereof will normally be administered systemically or partially; usually by oral or parenteral (e.g. intravenous, subcutaneous or intramuscular) administration.

Solid compositions for oral administration include compressed tablets, pills, dispersible powders and granules. In such solid compositions, one or more of the active compound(s) is, or are, admixed with at least one inert diluent such as lactose, mannitol, glucose, hydroxypropyl cellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, and disintegrating agents, such as cellulose calcium gluconate. The tablets or pills may, if desired, be made into enteric film-coated or gastric film-coated tablets or pills, such as sugar-coated, gelatin-coated, hydroxypropylcellulose-coated or hydroxypropylmethylcellulose phthalate-coated tablets or pills; two or more layers may be used.

The compositions for oral administration also include capsules of absorbable material such as gelatin, containing one or more of the active substances with or without the addition of diluents or excipients.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise at least one compound of the present invention.

Preparations for parenteral administration include sterile aqueous or non-aqueous solutions, suspensions or emulsions. Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol, and Polysorbate 80 (registered Trade Mark).

These compositions may also include adjuvants such as preserving, wetting, emulsifying and dispersing agents. They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Other compositions include, for parenteral administration, liquids for external use, and endermic liniments such as ointments; suppositories for rectal administration; and pessaries for vaginal administration. Such compositions are prepared by known methods.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance.

The dose to be administered is determined depending upon, for example, age, symptoms, the desired therapeutic effects, the route of administration, and the duration of the treatment.

In the human adult, the doses per person are generally between 0.1 and 100 μg, preferably between 1 and 50 μg by oral administration, and between 0.01 and 50 μg, preferably between 0.1 and 20 μg by parenteral administration in the prevention or treatment of cyto-damage, and can be administered up to several times per day. In particular the doses are preferably administered 3 or 4 times per day at a total daily dose of 0.4–400 μg per day. in the prevention or treatment of cyto-damage.

In domestic mammals, such as cows, mares, sows, ewes and bitches, the doses are generally between 0.1 and 100 μg per kg, preferably between 1 and 50 μg per kg by oral administration, and between 0.01 and 10 μg per kg, preferably 0.1 and 5 μg per kg, by parenteral administration in the treatment or prevention of cyto-damage, and can be administered 3 or 4 times per day.

As mentioned above, the doses to be used depend on various factors. Therefore, there may be cases in which doses greater than the ranges specified above, or lower than the ranges specified above, may be used.

The following Experiments and Examples illustrate biological activities and the preparation of pharmaceutical compositions of the compounds of general formula VA and VB.

EXPERIMENT 1

Effect on carbon tetrachloride (CCl$_4$) induced liver damage (liver cell necrosis type)

Male Wistar rats weighing 180–220 g were used. Rats were dosed intraperitoneally with CCl$_4$ dissolved in olive oil (5%, w/v) at a volume of 500 μl/kg after 18 hr starvation. The compound under test was administered orally (p.o.) or subcutaneously (s.c.) 6 and 12 hr after CCl$_4$ injection in rats and blood was collected after 24 hr. Plasma glutamic oxaloacetic transaminase (GOT) and glutamic pyruvic transaminase (GPT) activities were determined by ultraviolet absorbance methods (optimised method based on the recommendations of the Deutsche Gesellschaft für Klinische Chemie). The effects of the compounds tested were assessed by the inhibition rate in comparison with controls. Inhibition rate was calculated by the following formula.

$$\text{Inhibition (\%)} = \left(1 - \frac{\text{treated value}}{\text{control value}}\right) \times 100$$

The results obtained are shown in the following Tables 1A and 1B for compounds of the general formula:

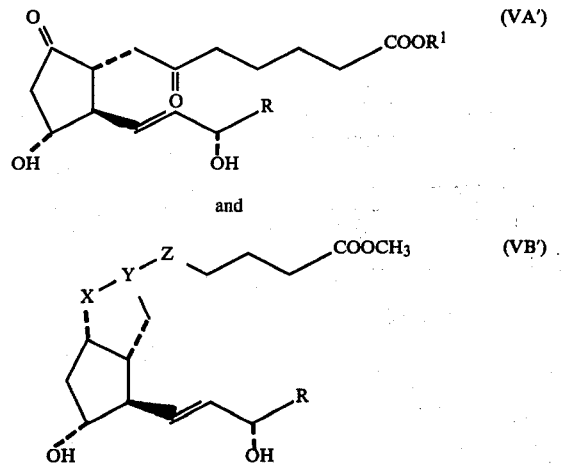

wherein R, R$^1$ and —X—Y—Z— have the meanings indicated.

In Tables 1A, 1B and 2 to 5 hereinafter the dose shown in the amount given at each administration of the compound under test.

TABLE 1A

| Compound No. | substituents in the formula VA' R | R$^1$ | route of administration | dose (μg/kg) | inhibition rate (%) GOT | GPT |
|---|---|---|---|---|---|---|
| 1 | ▱—C$_2$H$_5$ | —CH$_3$ | s.c. | 50 | 21.0 | 0 |
| 2 | ▱—C$_3$H$_7$ | —CH$_3$ | s.c. | 50 | 52.4 | 17.3 |
| 3 | △ | —CH$_3$ | p.o. | 100 | 19.0 | 30.5 |
| 4 | △—C$_3$H$_7$ | —CH$_3$ | p.o. | 100 | 77.0 | 51.5 |

TABLE 1A-continued

| Compound No. | substituents in the formula VA' R | R¹ | route of administration | dose (μg/kg) | inhibition rate (%) GOT | GPT |
|---|---|---|---|---|---|---|
| 5 | 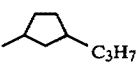 C₃H₇ | —H | p.o. | 100 | 32.6 | 44.5 |
| 6[1] | 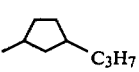 C₃H₇ | —CH₃ | p.o.<br>s.c. | 100<br>20 | 71.3<br>54.1 | 67.5<br>43.2 |
| 7 | 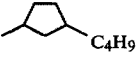 C₄H₉ | —CH₃ | p.o. | 100 | 62.7 | 55.1 |
| 8[2] | 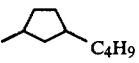 C₄H₉ | —CH₃ | p.o.<br>s.c. | 100<br>20 | 77.7<br>44.4 | 73.7<br>39.3 |
| 9 | 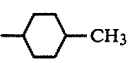—CH₃ | —CH₃ | p.o.<br>s.c. | 100<br>50 | 21.0<br>13.1 | 0<br>8.8 |
| 10 | 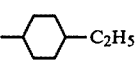—C₂H₅ | —CH₃ | s.c. | 50 | 35.6 | 12.2 |
| 11 | 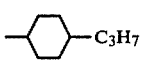—C₃H₇ | —CH₃ | s.c. | 50 | 48.5 | 45.1 |
| 12[3] | 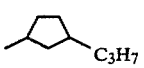 C₃H₇ | —CH₃ | p.o. | 100 | 25.4 | 22.2 |

TABLE 1B

| Compound No. | substituents in the formula (VB') R | X—Y—Z— | route of administration | dose (μg/kg) | inhibition rate (%) GOT | GPT |
|---|---|---|---|---|---|---|
| 13 | 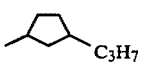 C₃H₇ | N=C—CH₂—<br>\| | p.o. | 1000 | 46.0 | 32.5 |
| 14[4] | 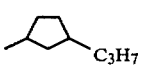 C₃H₇ | N=C—CH₂—<br>\| | p.o.<br>s.c. | 500<br>500 | 39.8<br>68.6 | 20.8<br>64.2 |
| 15 | 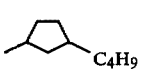 C₄H₉ | N=C—CH₂—<br>\| | p.o. | 1000 | 45.5 | 15.6 |
| 16 | 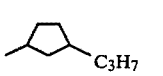 C₃H₇ | O—CH—CH₂—<br>\| | p.o. | 1500 | 51.0 | 53.0 |
| 17 | 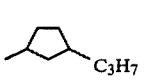 C₃H₇ | O—CH   CH₂—<br>\| | p.o. | 1000 | 32.9 | 32.0 |

In Tables 1A and 1B (1) Compound 6 is the less polar compound (Rf=0.18) separated from compound 4 by thin layer chromatography (abbreviated as TLC hereafter) (eluent; ethyl acetate:cyclohexane=5:1). Angle of rotation of this compound $[\alpha]_D^{20}$ was −76.6° at c=0.438 in chloroform solution.

(2) Compound 8 is the less polar compound (Rf=0.26) separated from compound 7 by TLC (eluent; ethyl acetate:cyclohexane=4:1). Angle of rotation of this compound $[\alpha]_D^{20}$ was −101.4° at c=0.434 in chloroform solution.

(3) Compound 12 is the more polar compound (Rf=0.14) separated from compound 4 by TLC (eluent; ethyl acetate:cyclohexane=4:1).

(4) Compound 14 is the less polar compound (Rf=0.12) separated from compound 13 by TLC (eluent; ethyl acetate:methanol=9:1). Angle of rotation of this compound $[\alpha]_D^{20}$ was −19.9° at c=1.00 in chloroform solution. The compounds for which results are given in Tables 1A and 1B are the following:

| Compound No. | names |
|---|---|
| 1 | 15-(3-Ethylcyclobutyl)-16,17,18,19 20-pentanor-6-oxo-PGE₁ methyl ester |
| 2 | 15-(3-Propylcyclobutyl)-16,17,18,19,20- |

-continued

| Compound No. | names |
|---|---|
|  | pentanor-6-oxo-PGE$_1$ methyl ester |
| 3 | 15-Cyclopentyl-16,17,18,19,20-pentanor-6-oxo-PGE$_1$ methyl ester |
| 4 | 15-(3-Propylcyclopentyl)-16,17,18,19,20-pentanor-6-oxo-PGE$_1$ methyl ester |
| 5 | 15-(3-Propylcyclopentyl)-16,17,18,19,20-pentanor-6-oxo-PGE$_1$ |
| 6 | 15-(3-Propylcyclopentyl)-16,17,18,19,20-pentanor-6-oxo-PGE$_1$ methyl ester (less polar) |
| 7 | 15-(3-Butylcyclopentyl)-16,17,18,19,20-pentanor-6-oxo-PGE$_1$ methyl ester |
| 8 | 15-(3-Butylcyclopentyl)-16,17,18,19,20-pentanor-6-oxo-PGE$_1$ methyl ester (less polar) |
| 9 | 15-(4-Methylcyclohexyl)-16,17,18,19,20-pentanor-6-oxo-PGE$_1$ methyl ester |
| 10 | 15-(4-Ethylcyclohexyl)-16,17,18,19,20-pentanor-6-oxo-PGE$_1$ methyl ester |
| 11 | 15-(4-Propylcyclohexyl)-16,17,18,19,20-pentanor-6-oxo-PGE$_1$ methyl ester |
| 12 | 15-(3-Propylcyclopentyl)-16,17,18,19,20-pentanor-6-oxo-PGE$_1$ methyl ester (more polar) |
| 13 | 15-(3-Propylcyclopentyl)-16,17,18,19,20-pentanor-6,9$\alpha$-nitrilo-PGI$_1$ methyl ester |
| 14 | 15-(3-Propylcyclopentyl)-16,17,18,19,20-pentanor-6,9$\alpha$-nitrilo-PGI$_1$ methyl ester (less polar) |
| 15 | 15-(3-Butylcyclopentyl)-16,17,18,19,20-pentanor-6,9$\alpha$-nitrilo-PGI$_1$ methyl ester |
| 16 | 15-(3-Propylcyclopentyl)-16,17,18,19,20-pentanor-PGI$_1$ methyl ester |
| 17 | (6S)-15-(3-propylcyclopentyl)-16,17,18,19,20-pentanor-PGI$_1$ methyl ester |

[Compounds 1–17, and the acids corresponding to compounds 1 to 3,6 and 9 to 17 are preferred compounds of formula VA and VB.]

EXPERIMENT 2

Effect on alcohol-induced acute liver damage

Male Wistar rats weighing 180–220 g were used. After the rats had fasted for 18 hr, 50% v/v ethanol solution was given orally to them at a volume of 12 ml/kg. The compound under test was administered orally 30 min before and 2 and 8 hr after administration of ethanol and blood was collected after 24 hr. Plasma GOT and GPT activities were determined in the manner described in Experiment 1. Effects were shown by the inhibition rate compared with controls (calculation by the formula shown in Experiment 1). The results obtained are shown in Table 2.

TABLE 2

| Effect on alcohol-induced acute liver damage | | | | |
|---|---|---|---|---|
| Compound No. | route of administration | dose ($\mu$g/kg) | inhibition rate (%) | |
|  |  |  | GOT | GPT |
| 6 | p.o. | 50 | 24.5 | 35.8 |

EXPERIMENT 3

Effect on D(+)-galactosamine hydrochloride-induced liver damage (hepatitis type)

Male Wistar rats weighing 180–220 g were used. After the rats had fasted for 18 hr, 250 mg/kg galactosamine hydrochloride was administered to them intraperitoneally three times at 4 hr intervals. The compound under test was administered orally 6, 12, 18, 24, 30, 36, 42 and 48 hr after the dose of D(+)-galactosamine hydrochloride and blood was collected after 36, 48 and 54 hr. Plasma GOT and GPT activities were determined in the manner described in Experiment 1 and the effects were shown by the inhibition rate compared with controls (calculation by the formula shown in Experiment 1).

The results obtained are shown in Table 3.

TABLE 3

| Effects on D(+)-galactosamine hydrochloride-induced liver damage | | | | | | | |
|---|---|---|---|---|---|---|---|
| Compound No. | route of administration | dose ($\mu$g/kg) | inhibition rates (%) | | | | |
|  |  |  | GOT | | | GPT | | |
|  |  |  | 36 hr after | 48 hr after | 54 hr after | 36 hr after | 48 hr after | 54 hr after |
| 6 | p.o. | 100 | 37.2 | 46.3 | 39.1 | 29.4 | 38.2 | 39.1 |

EXPERIMENT 4

Effect on p-acetoamidophenol-induced liver damage (liver glutathione decrease type)

Male Wistar rats weighing 180–220 g were used. After the rats had fasted for 18 hr, p-acetoamidophenol (2.5 g/kg) was given orally to them. The compound under test was administered orally 30 min before and 6 and 12 hr after administration of p-acetoamidophenol and blood was collected after 24 hr. Plasma GOT and GPT activities were determined in the manner described in experiment 1 and the results given in Table 4 show the inhibition rate compared with controls (calculation by the formula shown in Experiment 1)

TABLE 4

| Effects on p-acetoamidophenol-induced liver damage (liver glutathione decrease type) | | | | |
|---|---|---|---|---|
| Compound No. | route of administration | dose ($\mu$g/kg) | inhibition (%) | |
|  |  |  | GOT | GPT |
| 6 | p.o. | 50 | 33.2 | 60.4 |

EXPERIMENT 5

Effect on $\alpha$-naphthylisothiocyanate-induced liver damage (cholangioatresia type)

Male Wistar rats weighing 190–220 g were used. After rats had fasted for 18 hr, $\alpha$-naphthylisothiocyanate (ANIT) dissolved in olive oil (1.5% w/v) was given orally to them at 30 mg/kg body weight. The compound under test was administered orally 30 min before and 6 and 12 hr after administration of ANIT and blood was collected after 24 hr. Plasma GOT, GPT and bilirubin activities were determined and the results given in Table 5 show the inhibition rate compared with controls (calculation by the formula shown in Experiment 1).

TABLE 5

| Effects on $\alpha$-naphthylisothiocyanate-induced liver damage (cholangioatresia type) | | | | | |
|---|---|---|---|---|---|
| Compound No. | route of administration | dose ($\mu$g/kg) | inhibition (%) | | |
|  |  |  | GOT | GPT | bilirubin |
| 6 | p.o. | 20 | 14.6 | 5.4 | 18.2 |
|  |  | 50 | 44.6 | 49.8 | 24.9 |
|  |  | 100 | 67.8 | 63.6 | 50.5 |

EXPERIMENT 6

Effect on ethionine-induced acute pancreatitis

Male TCL-ICR mice from 4 weeks of age were used. After normal feeding the mice were given a choline-deficient diet (CD diet) for 2 days. Further after having fasted for 24 hr, they were given a choline-deficient diet containing 5% DL-ethionine (CDE diet) for 2 days, counted as days 1 and 2. The mice were then given the CD diet for 1 day and thereafter fed normally. Compound number 6 was administered subcutaneously to them at 5 µg/kg, twice daily, during the CDE diet on days 1 and 2, and then administered in the same manner once daily on days 3, 4 and 5. The effect of the compound under test on the survival rate at day 9 was determined. Further details of the test method appear in Gastroenterology, 78, 777 (1980).

Compound No. 6 conferred significant protection against death at day 9 from the administration of CDE diet. 12 of 16 untreated control mice were dead, whereas only 3 of 16 treated mice were dead.

EXPERIMENT 7

Acute toxicity test

Male JCL-ICR mice (non SPF mice) from 7 weeks of age were used. The compound under test was dissolved in 5% v/v ethanol containing 0.4% w/v Tween 80 (Tween is a registered trademark) and administered orally to the mice. The mice were observed for 14 days. The deaths observed were all within 72 hrs after treatment. The calculated $LD_{50}$ values are shown in Table 6.

TABLE 6

| Compound No. | $LD_{50}$ (mg/kg) |
|---|---|
| 3 | 10–20 |
| 6 | 10–20 |
| 8 | 10–20 |
| 14 | 40–100 |

As shown in Table 6, the toxicity of the compounds tested, representative of formula VA and VB is very low, ie the compounds are considered to be sufficiently safe and suitable for medical use.

The following Examples illustrate pharmaceutical compositions containing compounds of formula VA and VB.

EXAMPLE 1

3 mg of 15-(3-propylcyclopentyl)-16,17,18,19,20-pentanor-6-oxo-$PGE_1$ methyl ester (less polar isomer compound No. 6) dissolved in 10 ml of ethanol, 100 mg of magnesium stearate, 20 mg of silicon dioxide, 10 mg of talc, 200 mg of cellulose calcium gluconate (CCG) and microcrystalline cellulose were mixed and dried in conventional manner. Sufficient microcrystalline cellulose was added to obtain 10 g of mixture. After mixing well, the mixture was punched out in conventional manner to obtain 100 tablets each containing 30 µg of the active ingredient.

EXAMPLE 2

In the same manner as in Example 1, but using as active ingredient 3 mg of 15-(3-butylcyclopentyl)-16,17,18,19,20-pentanor-6-oxo $PGE_1$ methyl ester (less polar isomer compound No. 8), 100 tablets each containing 30 µg of the active ingredient were obtained.

EXAMPLE 3

In the same manner as in Example 1, but using as active ingredient 5 mg of 15-(3-propylcyclopentyl)-16,17,18,19,20-pentanor-6,9α-nitrilo-$PGI_1$ methyl ester (less polar isomer, compound No. 14), 100 tablets each containing 50 µg of the active ingredient were obtained.

EXAMPLE 4

To a mixture of 42 mg of α-cyclodextrin clathrate of 15-(3-propylcyclopentyl)-16,17,18,19,20-pentanor-6-oxo-$PGE_1$ methyl ester (less polar isomer, compound No. 6: content of the active ingredient was 3 mg), 100 mg of magnesium stearate, 20 mg of silicon dioxide, 10 mg of talc and 200 mg of CCG, microcrystalline cellulose was added to obtain 10 g of mixture. After mixing well, the mixture was punched out in conventional manner to obtain 100 tablets each containing 30 µg of the active ingredient.

EXAMPLE 5

To 42 mg of α-cyclodextrin clathrate of 15-(3-propylcyclopentyl)-16,17,18,19,20-pentanor-6-oxo-$PGE_1$ methyl ester (less polar isomer, compound No. 6; content of the active ingredient was 3 mg), lactose was added to obtain 21 g of mixture. After mixing well, the powder obtained was machine filled into 100 No. 3 gelatin capsules each containing 30 µg of the active ingredient.

EXAMPLE 6

In the same manner as in Example 5, using 60 mg of α-cyclodextrin clathrate of 15-(3-propylcyclopentyl)-16,17,18,19,20-pentanor-6,9α-nitrilo-$PGI_1$ methyl ester (less polar isomer, compound No. 14; content of the active ingredient was 5 mg), 100 capsules each containing 50 µg of the active ingredient were obtained.

EXAMPLE 7

A solution of 30 mg of 15-(3-propylcyclopentyl)-16,17,18,19,20-pentanor-6-oxo-$PGE_1$ methyl ester (less polar isomer, compound No. 6) dissolved in 10 ml of chloroform was added to 100 ml of MCT (a mixture of triglycerides of fatty acids containing from 8 to 10 carbon atoms) and the solution was mixed well. After removing chloroform under reduced pressure, the residue was machine filled into 100 soft capsules each containing 30 µg of the active ingredient.

EXAMPLE 8

6 mg of α-cyclodextrin clathrate of 15-(3-propylcyclopentyl)-16,17,18,19,20-pentanor-6-oxo-$PGE_1$ methyl ester (less polar isomer, compound No. 6) was dissolved in 300 ml of distilled water for injection. The solution was sterilized in conventional manner and placed in 3 ml portions in 5 ml ampoules to obtain 100 ampoules each containing 5 µg of the active ingredient.

EXAMPLE 9

In the same manner as in Example 8, but using 12 mg of α-cyclodextrin clathrate of 15-(3-propylcyclopentyl)-16,17,18,19,20-pentanor-6,9α-nitrilo-$PGI_1$ methyl ester (less polar isomer, compound No. 14), 100 ampoules each containing 10 µg of the active ingredient were prepared.

We claim:

1. A method for the prevention or treatment of cytodamage associated with liver, pancreatic or kidney disease in a mammalian host which comprises administering to a host subject to, or suffering from, an aforesaid an effective amount of a prostaglandin analogue of the general formula:

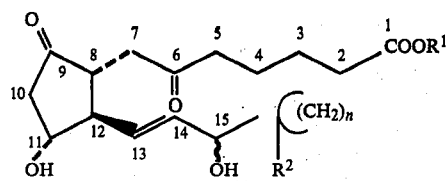

or

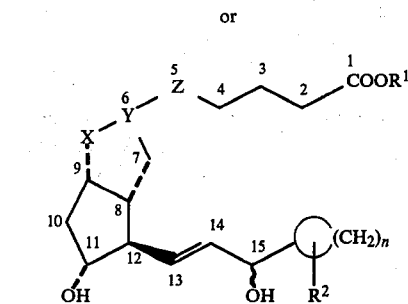

wherein $R^1$ represents a hydrogen atom or a straight- or branched-chain alkyl group containing from 1 to 12 carbon atom(s), $R^2$ represents a hydrogen atom or a straight- or branched-chain alkyl group containing from 1 to 6 carbon atom(s), the symbols ——X—Y—Z— in formula VB represent one of the groups:

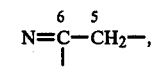 (i)

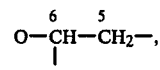 (ii)

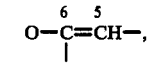 (iii)

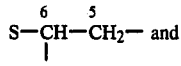 (iv)

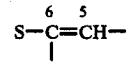 (v)

wherein in the formulae (ii) and (iv), the configuration on $C_6$ is S- or R-configuration or a mixture thereof, and in the general formulae (iii) and (v), the double bond between $C_5$ and $C_6$ is in E- or Z-configuration or a mixture thereof, and n represents an integer of from 3 to 5, the double bond between $C_{13}$–$C_{14}$ is trans, and the hydroxy group attached to $C_{15}$ is in $\alpha$- or $\beta$-configuration or a mixture thereof or, when $R^1$ represents a hydrogen atom, non-toxic salt thereof, or cyclodextrin clathrate thereof.

2. A method according to claim 1 in which the amount of prostaglandin analogue administered is from 0.1 to 100 μg per kg by oral administration or from 0.01 to 10 μg per kg by parenteral administration.

3. A method according to claim 1 in which the amount of prostaglandin analogue administered is from 0.1 to 100 μg by oral administration or from 0.01 to 50 μg by parenteral administration.

4. A method according to claim 1 in which the amount of prostaglandin analogue administered is from 1 to 50 μg by oral administration or from 0.1 to 20 μg by parenteral administration.

5. A method according to claim 1 in which a prostaglandin analogue of general formula VA depicted in claim 1 (wherein the various symbols are as defined in claim 1) or, when $R^1$ represents a hydrogen atom, non-toxic salt thereof or cyclodextrin clathrate thereof, is administered.

6. A method according to claim 5 in which the prostaglandin analogue is 15-(3-ethylcyclobutyl)-16,17,18,19,20-pentanor-6-oxo-$PGE_1$ or methyl ester thereof.

7. A method according to claim 5 in which the prostaglandin analogue is 15-(3-propylcyclobutyl)-16,17,18,19,20-pentanor-6-oxo-$PGE_1$ or methyl ester thereof.

8. A method according to claim 5 in which the prostaglandin analogue is 15-cyclopentyl-16,17,18,19,20-pentanor-6-oxo-$PGE_1$ or methyl ester thereof.

9. A method according to claim 5 in which the prostaglandin analogue is 15-(3-propylcyclopentyl)-16,17,18,19,20-pentanor-6-oxo-$PGE_1$ or methyl ester thereof.

10. A method according to claim 5 in which the prostaglandin analogue is the less polar isomer of 15-(3-propylcyclopentyl)-16,17,18,19,20-pentanor-6-oxo-$PGE_1$ or methyl ester thereof.

11. A method according to claim 5 in which the prostaglandin analogue is 15-(3-butylcyclopentyl)-16,17,18,19,20-pentanor-6-oxo-$PGE_1$ methyl ester.

12. A method according to claim 5 in which the prostaglandin analogue is the less polar isomer of 15-(3-butylcyclopentyl)-16,17,18,19,20-pentanor-6-oxo-$PGE_1$ methyl ester.

13. A method according to claim 5 in which the prostaglandin analogue is 15-(4-methylcyclohexyl)-16,17,18,19,20-pentanor-6-oxo-$PGE_1$ or methyl ester thereof.

14. A method according to claim 5 in which the prostaglandin analogue is 15-(4-ethylcyclohexyl)-16,17,18,19,20-pentanor-6-oxo-$PGE_1$ or methyl ester thereof.

15. A method according to claim 5 in which the prostaglandin analogue is 15-(4-propylcyclohexyl)-16,17,18,19,20-pentanor-6-oxo-$PGE_1$ or methyl ester thereof.

16. A method according to claim 5 in which the prostaglandin analogue is the more polar isomer of 15-(3-propylcyclopentyl)-16,17,18,19,20-pentanor-6-oxo-$PGE_1$ or methyl ester thereof.

17. A method according to claim 1, in which a prostaglandin analogue of general formula VB depicted in claim 1 wherein the various symbols are as defined in claim 1 or, when $R^1$ represents a hydrogen atom, non-toxic salt thereof or cyclodextrin clathrate thereof, is administered.

18. A method according to claim 17 in which, in the prostaglandin analogue of general formula VB the symbols ——X—Y—Z— represent a group of the formula ——N=C—$CH_2$—.

19. A method according to claim 18 in which the prostaglandin analogue is 15-(3-propylcyclopentyl)-

16,17,18,19,20-pentanor-6,9α-nitrilo-PGI$_1$ or methyl ester thereof.

20. A method according to claim 18 in which the prostaglandin analogue is the less polar isomer of 15-(3-propylcyclopentyl)-16,17,18,19,20-pentanor-6,9α-nitrilo-PGI$_1$ or methyl ester thereof.

21. A method according to claim 18 in which the prostaglandin analogue is 15-(3-propylcyclopentyl)-16,17,18,19,20-pentanor-6,9α-nitrilo-PGI$_1$ or methyl ester thereof.

22. A method according to claim 17 in which, in the prostaglandin analogue of general formula VB the symbols ———X—Y—Z— represent a group of the formula

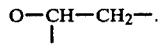

23. A method according to claim 22 in which the prostaglandin analogue is 15-(3-propylcyclopentyl)-16,17, 18,19,20-pentanor-PGI$_1$ or methyl ester thereof.

24. A method according to claim 22 in which the prostaglandin analogue is (6S)-15-(3-propylcyclopentyl)-16,17,18,19,20-pentanor-PGI$_1$ or methyl ester thereof.

25. A method according to claim 1 in which the disease is liver disease.

26. A method according to claim 1 in which the disease is pancreatic disease.

27. A method according to claim 1 in which the disease is kidney disease.

28. A method according to claim 25 in which the liver disease is acute yellow atrophy, fatty liver, hepatic coma, hepatitis, hepatolenticular disease, hepatomegaly, portal hypertension, obstructive jaundice, liver abscess, liver cirrhosis, parasitic liver diseases, liver neoplasms or hepatic tuberculosis.

29. A method according to claim 26 in which the pancreatic disease is pancreatitis.

30. A method according to claim 27 in which the kidney disease is diabetic nephropathies, kidney cortex necrosis, acute kidney failure or nephrosclerosis.

* * * * *